(12) United States Patent
Eriksson et al.

(10) Patent No.: US 11,020,615 B2
(45) Date of Patent: Jun. 1, 2021

(54) COMPUTING RADIOTHERAPY DOSE DISTRIBUTION

(71) Applicant: Elekta AB (publ), Stockholm (SE)

(72) Inventors: Markus Eriksson, Gustavsberg (SE); Jens Olof Sjölund, Sundbyberg (SE); Linn Öström, Lund (SE); David Andreas Tilly, Uppsala (SE); Peter Kimstrand, Uppsala (SE); Jonas Anders Adler, Stockholm (SE)

(73) Assignee: Elekta AB (publ), Stockholm (SE)

( * ) Notice: Subject to any disclaimer, the term of this patent is extended or adjusted under 35 U.S.C. 154(b) by 0 days.

(21) Appl. No.: 16/563,139

(22) Filed: Sep. 6, 2019

(65) Prior Publication Data

US 2020/0254277 A1 Aug. 13, 2020

Related U.S. Application Data

(60) Provisional application No. 62/804,981, filed on Feb. 13, 2019.

(51) Int. Cl.
*A61N 5/10* (2006.01)
*G06N 20/10* (2019.01)
*G06N 3/08* (2006.01)
*G06N 7/00* (2006.01)

(52) U.S. Cl.
CPC ......... *A61N 5/1031* (2013.01); *A61N 5/1039* (2013.01); *A61N 5/1048* (2013.01); *G06N 3/08* (2013.01); *G06N 7/005* (2013.01); *G06N 20/10* (2019.01); *A61N 2005/1034* (2013.01)

(58) Field of Classification Search
None
See application file for complete search history.

(56) References Cited

U.S. PATENT DOCUMENTS 10,765,890 B2 * 9/2020 Sun .......................... G06T 11/00
10,796,793 B2 * 10/2020 Zankowski ............ G16H 20/40
2007/0003011 A1 1/2007 Lane
(Continued)

FOREIGN PATENT DOCUMENTS

WO 9014129 11/1990
WO 2018048575 3/2018

OTHER PUBLICATIONS

Ahnesjö, Anders, et al., "Dose calculations for external photon beams in radiotherapy", Physics in Medicine & Biology 44.11, (1999), R99-R155.
(Continued)

*Primary Examiner* — Thomas R Artman
(74) *Attorney, Agent, or Firm* — Schwegman Lundberg & Woessner, P.A.; Sanjay Agrawal

(57) ABSTRACT

Systems and methods for calculating radiotherapy dose distribution are provided. The systems and methods include operations for receiving data representing at least one of particle trajectories or a dose deposition pattern in a simulated delivery of a radiotherapy plan; applying a dose calculation process to the received data to generate a first radiotherapy dose distribution having a first level of detail; and processing the first radiotherapy dose distribution using a trained machine learning technique to generate a second radiotherapy dose distribution having a second level of detail that enhances the first level of detail.

29 Claims, 7 Drawing Sheets

(56) References Cited

U.S. PATENT DOCUMENTS

| | | | |
|---|---|---|---|
| 2011/0065974 A1 | 3/2011 | Rietzel | |
| 2013/0030762 A1* | 1/2013 | Mercier | A61N 5/1031 |
| | | | 702/179 |
| 2018/0243586 A1* | 8/2018 | Ramezanzadeh Moghadam | |
| | | | G16H 20/40 |
| 2019/0051398 A1* | 2/2019 | Zankowski | G06N 5/02 |
| 2019/0074079 A1* | 3/2019 | Zankowski | G06K 9/6288 |
| 2019/0209867 A1* | 7/2019 | Sun | G16H 30/40 |
| 2020/0104695 A1* | 4/2020 | Laaksonen | A61N 5/1031 |
| 2020/0105394 A1* | 4/2020 | Laaksonen | A61N 5/1038 |
| 2020/0105399 A1* | 4/2020 | Laaksonen | G06N 3/08 |
| 2020/0171325 A1* | 6/2020 | Yang | A61N 5/1031 |
| 2020/0188692 A1* | 6/2020 | Liu | G06N 20/00 |
| 2020/0254277 A1* | 8/2020 | Eriksson | G06N 3/08 |

OTHER PUBLICATIONS

Lehtinen, Jaakko, et al., "Noise2noise: Learning image restoration without clean data", arXiv preprint arXiv:1803.04189, (2018), 12 pgs.

Madrigal, Jorge Asensi, "Deep learning approach for denoising Monte Carlo dose distribution in proton therapy", Diss. PhD thesis, UCL-Ecole polytechnique de Louvain, (2018), 90 pgs.

Maier, Joscha, et al., "Deep scatter estimation (DSE): feasibility of using a deep convolutional neural network for real-time x-ray scatter prediction in cone-beam CT", Medical imaging 2018: physics of medical imaging. vol. 10573. International Society for Optics and Photonics, (2018), 105731L-1-105731L-6.

Öström, Linn, "Post-processingof Monte Carlo calculated dose distributions", Diss. Master thesis, KTH Royal Institute of Technology, (2019), 71 pgs.

"European Application Serial No. 20157132.0, Extended European Search Report dated Jun. 9, 2020", 5 pgs.

* cited by examiner

COMPUTING RADIOTHERAPY DOSE DISTRIBUTION

CLAIM FOR PRIORITY

This application claims the benefit of priority to U.S. Provisional Application No. 62/804,981, filed Feb. 13, 2019, which is herein incorporated by reference in its entirety.

TECHNICAL FIELD

Embodiments of the present disclosure relate generally to radiation therapy or radiotherapy. More specifically, this disclosure relates to systems and methods for computing dose distribution in radiotherapy.

BACKGROUND

External beam radiotherapy is used to treat cancers and other ailments in mammalian (e.g., human and animal) tissue. External beam radiotherapy employs a radiotherapy device that creates a radiation beam of particles (photons, electrons, and/or ions) to irradiate a tumor in a patient. One such radiotherapy device is a Gamma Knife, which irradiates a patient with a large number of low-intensity gamma rays that converge with high intensity and high precision at a target (e.g., a tumor). External beam radiotherapy also includes linear particle accelerator (LINAC)-based radiotherapy and circular particle accelerators (e.g., cyclotron, synchrotron, and synchrocyclotron). Another form of radiotherapy is brachytherapy, where a radiation source is placed inside or next to the area requiring treatment. The direction and shape of the radiation beam should be accurately controlled to ensure the tumor receives the prescribed radiation dose, and the radiation from the beam should minimize damage to the surrounding healthy tissue, often called the organ(s) at risk (OAR 420s). Treatment planning is used to control radiation beam parameters, and a radiotherapy device effectuates a treatment by delivering a spatially varying dose distribution to the patient.

OVERVIEW

In some embodiments, a computer-implemented method, non-transitory computer-readable medium, and a system comprising a memory and processor are provided for performing operations including: receiving data representing at least one of particle trajectories or a dose deposition pattern in a simulated delivery of a radiotherapy plan; applying a dose calculation process to the received data to generate a first radiotherapy dose distribution having a first level of detail; and processing the first radiotherapy dose distribution using a trained machine learning technique to generate a second radiotherapy dose distribution having a second level of detail that enhances the first level of detail.

In some implementations, the computer-implemented method, non-transitory computer-readable medium, and the system further perform operations including generating a radiation dose distribution or treatment plan to perform an operation associated with a radiotherapy treatment device based on the second radiotherapy dose distribution, wherein the operation includes at least one of delivering radiotherapy using the radiotherapy treatment device or verifying proper operation of the radiotherapy treatment device in real-time during treatment.

In some implementations, the particle includes at least one of a photon, proton, electron or ion, and wherein the dose calculation process applied to generate the first radiotherapy dose distribution includes at least one or a combination of a Monte Carlo simulation or a deterministic calculation using a point kernel convolution algorithm, a pencil kernel algorithm, or a Boltzmann equation solver.

In some implementations, the data includes multiple single particle simulations, wherein the data includes at least one or a combination of a mean-free path parameter, interaction type parameter, deposited energy parameter, and wherein the particle trajectories represent post direction of travel sampled from one or more specified distributions or one or more distributions specified up to a specified value.

In some implementations, the dose calculation process includes a Monte Carlo simulation that is prematurely stopped before convergence to the second level of detail, where convergence is measured using a measure of statistical dispersion, and wherein the first dose distribution has a higher measure of statistical dispersion than the second dose distribution.

In some implementations, the dose calculation process comprises a point kernel convolution process that includes a ray trace step and a convolution step and the computer-implemented method, non-transitory computer-readable medium, and the system further perform operations including applying a dose calculation process to the received data, which comprises computing an amount representing a total energy released per unit mass in a patient based on the received data using a ray trace process; and without requiring performing the convolution step, modeling transport and dose deposition of photons and electrons generated by the incident photons, based on the trained machine learning technique to generate the second radiotherapy dose distribution.

In some implementations, the second radiotherapy distribution represents a dose from individual beamlets or shots.

In some implementations, the computer-implemented method, non-transitory computer-readable medium, and the system further perform operations including generating a complete dose plan based on the second radiotherapy dose distribution for a given radiotherapy machine configuration.

In some implementations, the second radiotherapy dose distribution represents an external radiation field associated with a radiotherapy treatment device and the computer-implemented method, non-transitory computer-readable medium, and the system further perform operations including determining an amount of radiation associated with the radiotherapy treatment device or treatment room; and based on the amount of radiation, performing at least one of estimating patient motion, configuring a radiation shield, or computing a beam model associated with the radiotherapy treatment device.

In some implementations, the machine learning technique comprises a neural network.

In some implementations, the neural network comprises at least one of a convolutional neural network and a denoising autoencoder, wherein the first radiotherapy dose distribution is represented as a three-dimensional image, and wherein processing the first radiotherapy dose distribution using the trained machine learning technique further comprises providing the first radiotherapy dose distribution, one or more additional radiotherapy dose distributions generated using the dose calculation process, patient geometry information, and beam setup information to the trained machine learning technique.

In some implementations, the dose calculation process comprises a point kernel convolution process, and wherein the trained machine learning technique is trained based on training data to establish a relationship between a computation representing total energy released per unit mass in a patient and a ground truth dose calculation.

In some implementations, the training data comprises sets of input-output data pairs, wherein the ground truth dose calculation is generated by applying the point kernel convolution process including a raytracing step and a convolution step to the training data set, and wherein the input portion of the input-output data pairs comprises a patient model.

In some implementations, the machine learning technique is trained to establish the relationship based on a single beam and is subsequently further trained to establish the relationship based on multiple beams.

In some implementations, the dose calculation process comprises a Monte Carlo process, and wherein the trained machine learning technique is trained based on training data to establish a relationship between a partial simulation result of the Monte Carlo process and a full simulation result of the Monte Carlo process.

In some implementations, the dose calculation process is performed for the absence of a magnetic field, and wherein the trained machine learning technique is trained based on training data to establish a relationship between the dose calculation process performed for the absence of a magnetic field and the dose calculation process performed for the presence of the magnetic field.

In some implementations, the dose calculation process includes a differentiable process, and wherein the machine learning technique comprises a differentiable machine learning technique.

In some implementations, the first level of detail represents at least one of or a combination of a first level of noise, a suboptimal input image, or a dose distribution in the absence of a magnetic field, and wherein the second level of detail represents at least one or a combination of a second level of noise less than the first level of detail, an improved input image or the dose distribution in the presence of a magnetic field.

In some embodiments, a computer-implemented method, non-transitory computer-readable medium, and a system comprising a memory and processor are provided for performing operations including: receiving a first radiotherapy dose distribution having a first level of detail, the first radiotherapy dose distribution being computed based on application of a dose calculation process to data representing at least one of particle trajectories or a dose deposition pattern in a simulated delivery of a radiotherapy plan; and training a machine learning technique to establish a relationship between the first radiotherapy dose distribution having the first level of detail and a radiotherapy dose distribution having a second level of detail that enhances the first level of detail.

In some implementations, the machine learning technique is trained based on training data to establish a relationship between one or a combination of a computation representing total energy released per unit mass in a patient and a ground truth dose calculation; a partial simulation result of a Monte Carlo process and a full simulation result of the Monte Carlo process; and the dose calculation process performed for the absence of a magnetic field and the dose calculation process performed for the presence of the magnetic field.

In some implementations, the first level of detail represents at least one of or a combination of a first level of noise, a suboptimal input image, or a dose distribution in the absence of a magnetic field, and wherein the second level of detail represents at least one or a combination of a second level of noise less than the first level of detail, an improved input image or the dose distribution in the presence of a magnetic field.

In some implementations, the machine learning technique is trained by: obtaining a training data pair comprising a training radiotherapy dose distribution having the first level of detail and a corresponding ground truth radiotherapy dose distribution having the second level of detail; processing the training radiotherapy dose distribution having the first level of detail with the machine learning technique to generate an estimate of the training radiotherapy dose distribution having the second level of detail; computing a deviation between the estimate of the training radiotherapy dose distribution having the second level of detail and the ground truth radiotherapy dose distribution having the second level of detail; and updating parameters of the machine learning model based on the computed deviation.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
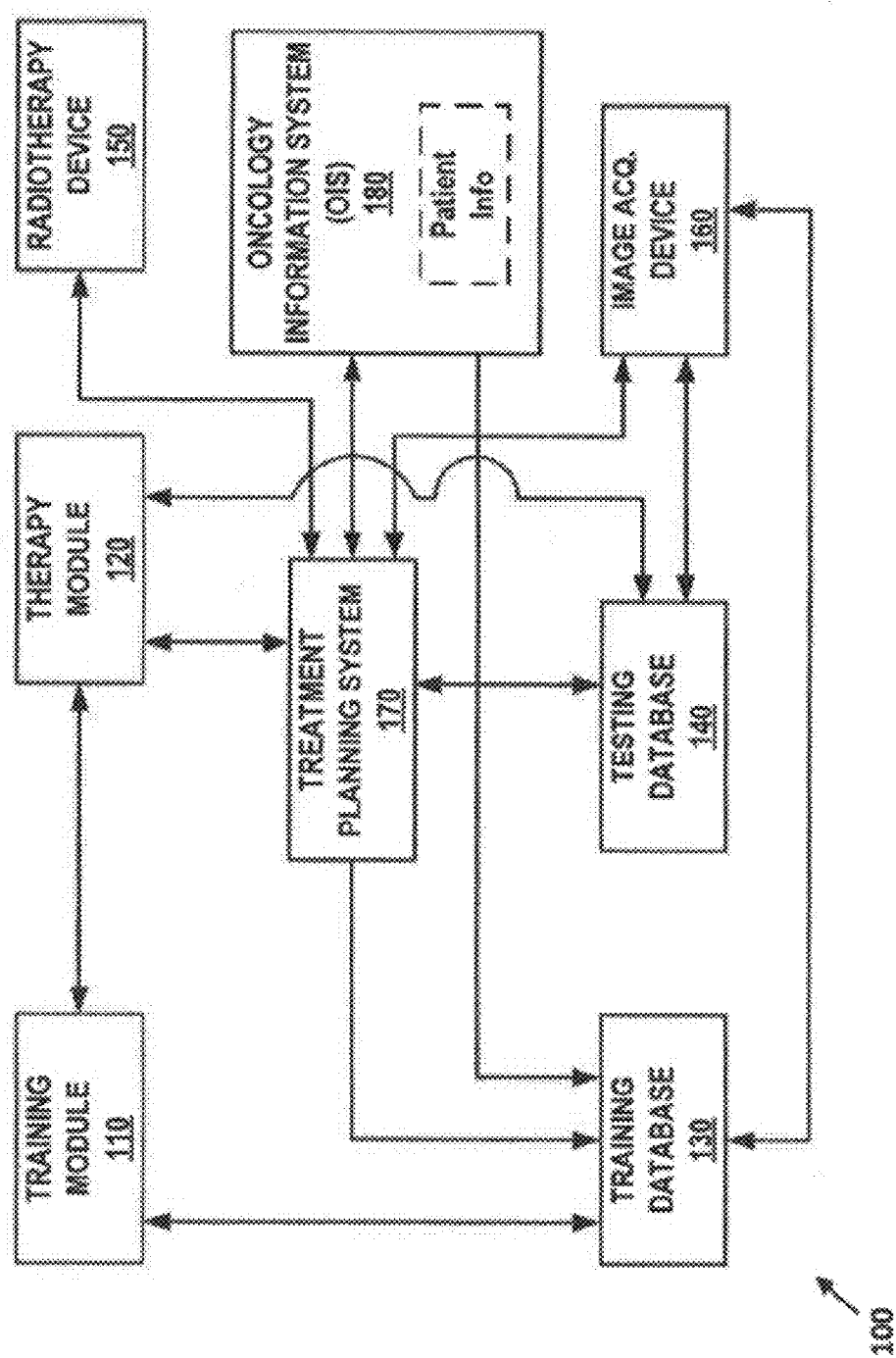
FIG. 1 illustrates an illustrative radiotherapy system adapted for performing treatment plan generation processing, according to some examples.

Systems and methods consistent with the present disclosure are directed to generating a dose distribution or treatment plan and/or validating a dose distribution or treatment plan that is both accurate and quickly generated using machine learning techniques (e.g., deep learning algorithms).

Simulation of radiation transport—dose calculation for short—is a cornerstone both for planning radiotherapy treatments and for designing radiotherapy equipment. Depending on the specific application there are different requirements on the accuracy of the dose calculation as well as the available computation time. These requirements are often conflicting, which makes it necessary to sacrifice one in favor of the other. For example, the optimization problems used in inverse treatment planning often requires recalculating the dose on the order of 100 times. To get acceptable solution times it is thus necessary to perform very fast, and thus quite crude, dose calculations using e.g. pencil kernel methods. In contrast, when calculating radiation leakage for the purpose of designing radiation shielding, very time-consuming Monte Carlo based dose calculations are necessary to achieve acceptable accuracy, and consequently such simulations have to run for days on expensive computing clusters. Further, the presence of a strong magnetic field, such as in the MR-linac, renders many of the widely used kernel-based dose calculation algorithms invalid. The only dose calculation alternatives are the ones based on Monte Carlo, but, it's not yet ascertained whether such methods are fast enough to be used as a real-time quality assurance (QA) tool, or in real-time adaptations of the treatment based on intra-fraction accumulated dose.

One way of speeding up Monte Carlo dose calculations involves halting the simulation prematurely, resulting in a noisy version of the dose distribution. Attempting to denoise it using analytical approaches, such as median filtering, may have adverse effects, such as removing or smudging actual features of the dose distribution, not related to noise.

Deterministic analytical dose calculations can be divided into two types: point kernel convolution algorithms and pencil kernel algorithms. Point kernel methods first calculate the total energy released per mass (TERMA) in the patient with a raytrace method and a subsequent convolution (or superposition) with the point kernel to model the dose distribution from the generated electrons and scattered photons. The convolution with the point kernel redistributes the TERMA into the correct dose distribution and is the most time-consuming step. A common implementation of the convolution step is the collapsed cone algorithm.

The Boltzmann transport equation (BTE) is the governing equation which describes the macroscopic behavior of radiation particles (neutrons, photons, electrons, etc.) as they travel through and interact with matter. The LBTE is the linearized form of the BTE, which assumes that radiation particles only interact with the matter they are passing through, and not with each other, and is valid for conditions without external magnetic fields. For a given volumetric domain of matter, subject to a radiation source, under the above conditions, the solution to the LBTE would give an "exact" description of the dose within the domain. However, since closed form solutions (analytic solutions) to the LBTE can only be obtained for a few simplified problems, the LBTE is typically solved in an open form, or non-analytic, manner. There are two general approaches to obtaining open form solutions to the LBTE. The first approach is the widely known Monte Carlo method. Monte Carlo methods do not explicitly solve the LBTE; they indirectly obtain the solution to this equation. The second approach is to explicitly solve the LBTE using numerical methods.

The disclosed embodiments include systems and methods for computing radiotherapy dose distribution (e.g., for creating a radiotherapy treatment plan ("treatment plan")) using an improved radiotherapy dose distribution calculation technique. The dose distribution calculation can be used to control delivery of radiotherapy by a radiotherapy device and/or to verify proper operation (perform quality assurance tests) of the radiotherapy device (e.g., to determine whether the actual dose delivered matches a calculated distribution within a threshold) in real-time or near real-time during treatment of a patient. The dose distribution calculation technique uses a machine learning technique (e.g., a neural network) that receives one or several dose calculation results (optionally in combination with patient geometry and beam setup) and outputs an accurate dose distribution. The input dose calculations may be a short (and noisy) Monte Carlo simulation, an approximate deterministic dose calculation (e.g., pencil kernel or collapsed cone or some relevant partial calculation thereof), or any combination thereof. A ground truth is also utilized to learn the desired output or train the machine learning technique. Such a ground truth may be obtained based on a long Monte Carlo simulation and/or physical measurements. In some implementations, the ground truth itself may be noisy provided that the input and output are sufficiently independent. In some embodiments, the short Monte Carlo simulation is calculated based on a Monte Carlo simulation that is prematurely stopped to output a dose distribution with a first level of detail before convergence to a dose distribution with a second level of detail. Convergence is measured using a measure of statistical dispersion, such that the first dose distribution has a higher measure of statistical dispersion than the second dose distribution.

The disclosed techniques may be applied on the level of individual beamlets/shots used in the dose distribution calculation. This enables fast creation of an accurate dose matrix, i.e. a linear map from a set of optimization variables to the dose in a set of voxels, which can then be used in current treatment plan optimization schemes (e.g., fluence map optimization). The disclosed techniques may be applied on complete dose distribution plans (e.g., the total dose distribution for a given machine configuration). If the input dose distribution calculation is provided by a differentiable algorithm, a differentiable machine learning technique can be employed to perform end-to-end differentiation of the composition. Namely, the machine learning technique itself is used in the treatment plan optimization. In some implementations, the disclosed techniques can be used to estimate motion in interventional X-ray imaging or planar X-ray imaging. Specifically, the disclosed techniques can be used to determine an amount of dose absorbed by an x-ray detector and, based on the amount of dose absorbed by the x-ray detector, estimating patient motion. In another implementation, the disclosed techniques can be used to estimate the radiation exposure (fluence) in various parts of the radiotherapy device and/or treatment room and, based on the estimated radiation exposure, design appropriate radiation shielding, or computing a beam model associated with the radiotherapy treatment device.

In some embodiments, the disclosed techniques are applied by exchanging the point kernel convolution step with a machine learning technique. The TERMA is computed in a typical manner but the convolution (superposition) step is replaced with a prediction step. The training set, in this case, consists of TERMA distributions and the corresponding full dose calculation. In order to correctly model the dose in areas of density heterogeneity, the patient model is used as input to the training set. This can be performed in increasing complexity by starting with dose distributions for single beam directions, to beams from multiple directions.

In some embodiments, the disclosed techniques model the curved trajectories of the electrons caused by the Lorentz force in the presence of magnetic field (which makes the dose distribution asymmetric and causes the electron return effect (ERE) at air-tissue interfaces). Specifically, a machine learning technique is used to correct for these effects, based on a dose distribution calculated without considering the magnetic field. The input includes dose distributions calculated without the magnetic field using any dose calculation process (e.g., pencil kernel/point kernel methods, or Monte Carlo), and the output is the corresponding dose distribution calculated with the magnetic field. In order to model the ERE at interfaces between low and high density materials, the input may include the patient model. This embodiment could generate a fast dose calculation algorithm that could be used as a secondary dose calculation QA-tool in the workflow for a radiotherapy device that is combined with a magnetic resonance imaging (MRI) device.

In some embodiments, the two embodiments above (e.g., replacing the point kernel convolutional step with a machine learning technique and correcting for magnetic field effects using a machine learning technique) can be combined to compute a dose distribution. For example, the machine learning technique can be applied to go directly from a TERMA distribution to a dose distribution that includes the effect of the magnetic field.

FIG. 1 illustrates an illustrative radiotherapy system 100. In some embodiments, radiotherapy system 100 includes a training module 110, a therapy module 120, a training database 130, a testing database 140, a radiotherapy device 150, and an image acquisition device 160. In some examples, radiotherapy system 100 includes a treatment planning system (TPS) 170 and an oncology information system (OIS) 180, which can provide patient information. In addition, radiotherapy system 100 may include output device(s) and input device(s). The output device(s) can be a display, printer, speaker, CD-writer, or another device that provides output from radiotherapy system 100. The input device(s) can be a touch input device such as a keyboard, mouse, pen, or trackball, a voice input device, a scanning device, or another device that provides input to the radiotherapy system 100. For audio, the input device(s) may be a sound card or similar device that accepts audio input in analog or digital form, or a CD-ROM reader that provides audio samples to the radiotherapy system 100.

Interconnections shown between elements are for illustrative purposes only. An interconnection mechanism such as a bus, controller, or network can interconnect the components of the radiotherapy system 100. Other connections can be available between elements not shown to be connected. Interconnections enable communication over a communication mechanism to storage devices (e.g., training database 130 and testing data 140) and/or computing entities (e.g., training module 110, therapy module 120, treatment planning system 170, radiotherapy device 150, image acquisition device 160, and/or OIS 180). The communication mechanism may convey information such as computer-executable instructions, audio/video or other information, or other data. By way of example, and not limitation, communication mechanisms include wired or wireless techniques implemented with an electrical, optical, RF, infrared, acoustic, or other carrier to communicate to another device, such as a memory bus interface, a processor bus interface, an Internet connection, a disk controller, and the like. The communication mechanisms can be configured by providing configuration parameters and/or sending signals to prepare the communication interface to provide a data signal describing the software content. The communication mechanisms can be accessed via one or more commands or signals sent to the communication interface.

As shown in FIG. 1, training module 110 may communicate with training database 130 to receive training data. Training database 130 may obtain training data from a treatment planning system 170, which may store data of previous radiotherapy treatment sessions (e.g., treatment planning system 170 stores previously developed treatment plans for a particular patient to be treated and for other patients, as well as other radiotherapy information). For example, treatment planning system 170 may provide information about a particular dose to be applied to a patient and other radiotherapy related information (e.g., type of therapy: such as image guided radiation therapy (IGRT), intensity modulated radiation therapy (IMRT), stereotactic radiotherapy; the number of beams; the beam angles; the dose per beam; energy spectrum of the particles; and the like). This information may include data representing particle trajectories in simulated delivery of a radiotherapy dose. The data may include interaction cross sections between projectile particle and medium, or derivatives thereof. This data will describe the modelling of particle trajectories or the generalized dose deposition of a particle. For example, the data representing particle trajectories may include multiple single photon, proton, and/or ion simulations and at least one of a mean-free path parameter, interaction type parameter, deposited energy parameter, and wherein the trajectories represent post direction of travel sampled from one or more specified distributions or one or more distributions specified up to a specified value.

In addition, the training data can also include image data to be obtained from image acquisition device 160. Image acquisition device 160 can include an MRI imaging device, a CT imaging device, a PET imaging device, an ultrasound device, a fluoroscopic device, a SPECT imaging device, or other medical imaging devices for obtaining one or more medical images of a patient. Image acquisition device 160 can provide the medical images to treatment planning system 170, testing database 140, and/or training database 130. For example, image acquisition device 160 can provide medical images (e.g., magnetic resonance imaging (MRI) images, 3D MRI, 2D streaming MRI, 4D volumetric MRI, computed tomography (CT) images, cone-beam CT, positron emission tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of a patient. In some embodiments, the training data can be collected from an OIS 180 (e.g., patient information, medical lab results, and the like).

The therapy module 120 may receive the data representing particle trajectories in a simulated delivery of a radiotherapy dose (e.g., incident energy of the therapy beam or interaction data for the particle and medium) and may calculate quickly and accurately an estimated dose distribution for the plan. The therapy module 120 may calculate the estimated dose distribution for the plan in two phases. In a first phase, the therapy module 120 applies a dose calculation process to the received data to generate a first radiotherapy dose distribution having a first level of detail. The dose calculation process may include any combination of a Monte Carlo simulation, a point kernel convolution process, or a pencil kernel process. The therapy module 120 may then obtain one or more trained machine learning techniques from the training module 110 to enhance the first radiotherapy dose distribution that is generated. Specifically, the therapy module 120 processes the first radiotherapy dose distribution using a trained machine learning technique to generate a second radiotherapy dose distribution having a second level of detail that enhances the first level of detail. The therapy module 120 generates a radiation dose distribution based on the second radiotherapy dose distribution.

The training module 110 may train one or more machine learning techniques which may be of different types and output the trained machine learning technique to therapy module 120. Each machine learning technique is trained by the training module 110 to establish different relationships between inputs and outputs in training data. Once the machine learning techniques are trained, new data can be received and applied to the trained machine learning technique to produce an expected set of outputs.

For example, the trained machine learning technique may be trained based on training data to establish a relationship between a computation representing total energy released per unit mass in a patient and a ground truth dose calculation that is generated by applying a point kernel convolution process consisting of calculating the total energy released per unit mass in a patient and a subsequent point kernel convolution step to the training data set. In this case, when only a total released energy in a patient (e.g., a new total released energy calculation) is received by the trained machine learning technique from a given dose calculation process (e.g., a point kernel convolution process), the trained machine learning technique estimates the corresponding dose calculation that is close to the ground truth dose calculation that includes the convolution step. Particularly, the point kernel convolution process can be applied to a set of data without applying the convolution step to generate a first radiotherapy treatment dose having a first level of detail. Then the therapy module 120, using the trained machine learning technique, processes the first radiotherapy treatment dose distribution to generate a second radiotherapy treatment dose distribution having a second level of detail that, for example, is an estimate of applying the convolution step of the point kernel convolution process.

As another example, the trained machine learning technique may be trained based on training data to establish a relationship between a partial simulation result of the Monte Carlo process and a full simulation result of the Monte Carlo process. In this case, when noisy dose calculations are received by the trained machine learning technique from a given dose calculation process (e.g., a Monte Carlo simulation that was terminated prematurely, such as before convergence to a dose calculation having the second level of detail), the trained machine learning technique estimates the corresponding dose calculation that is close to the full Monte Carlo simulation on the data and is less noisy (e.g., the Monte Carlo simulation that converges to provide a dose calculation with the second level of detail). Particularly, the Monte Carlo simulation can be applied to a set of data and terminated prematurely to generate a first radiotherapy treatment dose distribution having a first level of detail (e.g., data that is suboptimal and noisy). Then the therapy module 120, using the trained machine learning technique, processes the first radiotherapy treatment dose distribution to generate a second radiotherapy treatment dose distribution having a second level of detail that, for example, is an estimate of applying the full Monte Carlo simulation that denoises the data. In such implementations, the machine learning technique may include a neural network (e.g., a convolutional neural network and/or a denoising autoencoder).

As another example, the trained machine learning technique may be trained based on training data to establish a relationship between the dose calculation process performed in the absence of a magnetic field and the dose calculation process performed in the presence of the magnetic field. In this case, when dose calculations are received by the trained machine learning technique from a given dose calculation process (e.g., a Monte Carlo algorithm) and/or from an output of another trained machine learning technique that has denoised the dose calculation provided by a given dose calculation process, the trained machine learning technique estimates the corresponding dose distribution calculation in the presence of a magnetic field.

In some implementations, patient geometry information, beam setup information, a patient model and/or a radiotherapy machine model may be provided during training to train the machine learning technique(s).

In an example, the image acquisition device 160 may be integrated with the treatment device as a single apparatus (e.g., a MRI device combined with a linear accelerator, also referred to as an "MRI-Linac"). Such an MRI-Linac can be used, for example, to determine a location of a target organ or a target tumor in the patient, so as to direct radiation therapy accurately, according to the radiation therapy treatment plan, to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like. In such cases, the machine learning technique that is trained to establish the relationship between dose calculations in the absence of a magnetic field and dose distribution calculations in the presence of a magnetic field can be applied to a given dose distribution calculation to enhance the level of detail.

The image acquisition device 160 can be configured to acquire one or more images of the patient's anatomy for a region of interest (e.g., a target organ, a target tumor or both). Each image, typically a 2D or 3D image or slice, can include one or more parameters (e.g., a 2D slice thickness, an orientation, and a location, etc.). In an example, a 3D image can be acquired to perform dose distribution calculation. The 3D image can be used to verify proper operation of the radiotherapy device 150 to determine whether a delivered or simulated delivery of a dose matches a calculated dose distribution.

In some embodiments, training module 110 and therapy module 120 may constitute a single data processing device. For example, training module 110 and therapy module 120 can be implemented as one or more software programs operating on the same hardware device. Similarly, training database 130 and testing database 140 can be implemented as a single database. For example, a single database can store both the training data and testing data 140. It is contemplated that any one of training module 110, therapy module 120, training database 130, and testing database 140 can be implemented as a standalone module.

In some embodiments, radiotherapy device 150 may be local with respect to therapy module 120. For example, radiotherapy device 150 and therapy module 120 can be located in the same room of a medical facility/clinic. In other embodiments, radiotherapy device 150 may be remote with respect to therapy module 120 and the data communication between radiotherapy device 150 and therapy module 120 via the treatment planning system 170 can be carried out through a network (e.g., a local area network (LAN); a wireless network; a cloud computing environment such as software as a service, platform as a service, infrastructure as a service; a client-server; a wide area network (WAN); and the like). Similarly, the communication links between other modules and/or devices can also be implemented in a local or remote manner.

In some embodiments, the techniques and solutions described herein can be performed by software, hardware, or both of a computing environment, such as one or more computing devices. For example, computing devices include server computers, desktop computers, laptop computers, notebook computers, handheld devices, netbooks, tablet devices, mobile devices, PDAs, special purpose imaging devices, graphics processing units (GPUs), tensor processing units (TPU), application-specific integrated circuits (ASIC), field-programmable gate arrays (FPGA) and other types of computing devices.

A suitable computing environment in which the described technologies, such as those described for FIG. 1, can be implemented include general-purpose or special-purpose computing environments. For example, the disclosed training module 110, therapy module 120, and/or treatment planning system 170 may be implemented using a computing device comprising a processing unit, memory, and storage storing computer-executable instructions. The disclosed technologies can also be implemented with other computer system configurations, including hand held devices, multiprocessor systems, microprocessor-based or programmable consumer electronics, network PCs, mini-computers, mainframe computers, a collection of client/server systems, and the like. The disclosed technologies can also be practiced in distributed computing environments where tasks are performed by remote processing devices that are linked through a communications network. In a distributed computing environment, program modules may be located in both local and remote memory storage devices.

The processing unit included, for example, in training module 110, therapy module 120, and/or treatment planning system 170 may execute computer-executable instructions and may be a real or a virtual processor device. In a multi-processing system, multiple processing units execute computer-executable instructions to increase processing power. The memory can be volatile memory (e.g., registers, cache, RAM), non-volatile memory (e.g., ROM, EEPROM, flash memory, etc.), or some combination of the two. The memory can store software implementing any of the technologies described herein. For example, the memory can store an operating system, training software implementing training module 110, and/or therapy software implementing therapy module 120. Typically, operating system software provides an operating environment for other software executing in the computing environment, and coordinates activities of the components of the computing environment.

The computing environment may have additional features. For example, the computing environment can include computer-readable storage devices. Computer-readable storage devices may be removable or non-removable, and include magnetic disks, magnetic tapes or cassettes, CD-ROMs, CD-RWs, DVDs, or any other tangible, computer-readable media, which can be used to store information and which can be accessed within the radiotherapy system 100. The computer-readable storage devices can store software containing instructions for any of the technologies described herein (e.g., training module 110, therapy module 120, and treatment planning system 170).

Disclosed embodiments may implement computer-executable instructions, such as those included in program modules and executed in a computing environment on a target real or virtual processor device. Program modules may include routines, programs, libraries, objects, classes, components, data structures, etc., that perform particular tasks or implement particular abstract data types. The functionality of the program modules may be combined or split between program modules as desired in various embodiments. Computer-executable instructions for program modules may be executed on a processing unit, as described above.

Various operations or functions of the example embodiments can be implemented as software code or instructions. Such content can be directly executable ("object" or "executable" form), source code, or difference code ("delta" or "patch" code). Software implementations of the embodiments described herein can be provided via an article of manufacture with the code or non-transitory instructions stored thereon, or via a method of operating a communication interface to send data via the communication interface. A machine or computer-readable storage device can cause a machine to perform the functions or operations described, and includes any mechanism that stores information in a tangible form accessible by a machine (e.g., computing device, electronic system, and the like), such as recordable/non-recordable media (e.g., read only memory (ROM), random access memory (RAM), magnetic disk storage media, optical storage media, flash memory devices, and the like). Computer-readable storage devices store computer-readable instruction in a non-transitory manner and do not include signals per se.

With reference to FIG. 1, training module 110 may use training data to generate an output (e.g., a training model). Training data may include a plurality of previous treatment plans. In some embodiments, training data can be stored in training database 130. For example, the stored training data can include past radiotherapy treatments, diagnostic images, treatment images (dose maps), segmentation information, and the like, associated with one or more previous treatment plans. The training data can include a plurality of training samples. In some embodiments, a training sample includes a feature vector and a corresponding target vector.

In some embodiments, the feature vector can include arbitrary dimension and/or multiple types of data (e.g., continuous, ordinal, discrete, and the like). In some embodiments, the feature vector can include a distance to predetermined anatomical regions, such as the planning target volume(s) (PTV) or the OAR 420($s$) or the patient's surface. In some examples, the feature vector can include a signed distance between a volume (e.g., a voxel) and an anatomical region, such as a PTV or the surface of the body part in the medical image, which can also be represented as voxels. Distances to multiple regions of interest can also be included in the feature vector. In some embodiments, the feature vector can include global information, such as spatial coordinates of an anatomical region or a probability that an anatomical region includes a particular tissue type. In some embodiments, the feature vector can include features derived from a convolution of images with at least one linear filter (e.g., local phase, gradients, edge, or corner detectors). In some embodiments, the feature vector can include features derived by a transformation of one or more images (e.g., Fourier transform, Hilbert transform, Radon transform, distance transform, discrete cosine transform, wavelet transform, and the like). In each of these embodiments described above regarding the feature vector, a corresponding transformation to an output probability density can be applied.

In some embodiments, the feature vector can include information based on "information theoretical measures" (e.g., mutual information, normalized mutual information, entropy, Kullback-Leibler distance, and the like). In some embodiments, the feature vector can include a feature descriptor providing a higher-dimensional representation as used in the field of computer vision, such feature descriptor may include characteristics of a particular voxel of the image, such as SIFT (Scale-invariant feature transform), SURF (speeded up robust features), GLOH (gradient location and orientation histogram), or HOG (histogram of oriented gradients). In another embodiment, the covariance/correlation between a plurality of image regions (e.g., two or more voxels) can be captured using a higher-dimensional representation. In some embodiments, the feature vector can include, for example, patient information such as age, gender, tumor size, a responsible physician and the like.

In another embodiment, the feature element can include patient specific information, responsible physician, organ or volume of interest segmentation data, functional organ modeling data (e.g., serial versus parallel organs, and appropriate dose response models), radiation dosage (e.g., also including dose-volume histogram (DVH) information), lab data (e.g., hemoglobin, platelets, cholesterol, triglycerides, creatinine, sodium, glucose, calcium, weight), vital signs (blood pressure, temperature, respiratory rate and the like), genomic data (e.g., genetic profiling), demographics (age, sex), other diseases affecting the patient (e.g., cardiovascular or respiratory disease, diabetes, radiation hypersensitivity syndromes and the like), medications and drug reactions, diet and lifestyle (e.g., smoking or non-smoking), environmental risk factors, tumor characteristics (histological type, tumor grade, hormone and other receptor status, tumor size, vascularity cell type, cancer staging, gleason score), previous treatments (e.g., surgeries, radiation, chemotherapy, hormone therapy), lymph node and distant metastases status, genetic/protein biomarkers (e.g., such as MYC, GADD45A, PPM1D, BBC3, CDKN1A, PLK3, XPC, AKT1, RELA, BCL2L1, PTEN, CDK1, XIAP, and the like), single nucleotide polymorphisms (SNP) analysis (e.g., XRCC1, XRCC3, APEX1, MDM2, TNFR, MTHFR, MTRR, VEGF, TGFβ, TNFα), texture descriptors (e.g., representations learned from deep learning), and the like. The feature vector can include one or more such feature elements, regardless of whether these feature elements are related to each other or not. In other words, the feature vector is predictive of the target vector.

With reference to FIG. 1, therapy module 120 can use the one or more training models to determine a therapy model, (e.g., distribution parameters or other properties or outcomes) to generate a new treatment plan. In some embodiments, therapy module 120 can receive the one or more training models from training module 110. In some embodiments, therapy module 120 can receive testing data from testing database 140. Testing data can include a plurality of testing samples (e.g., elements). In some embodiments, a testing sample includes a feature vector (e.g., descriptive feature), as described herein. For example, the feature vector can be descriptive of the testing data, including information such as signed distance from a PTV to an OAR 420. In some embodiments, testing data can include place holders for target elements indicating an unobserved outcome corresponding to a feature element in testing data.

The testing data stored, for example, in testing database 140, can further include image data that may be obtained from image acquisition device 160. For example, image acquisition device 160 can provide medical images (e.g., MRI images, CT images, PET images, X-ray images, ultrasound images, radiotherapy portal images, single-photo emission computed tomography (SPECT) images, and the like) of a patient.

The testing data and other radiotherapy information stored in testing database 140 can also be obtained from treatment planning system 170 and/or oncology information system 180. Testing data can be stored in testing database 140 before being received by therapy module 120.

Alternatively, during adaptive radiotherapy, the testing data can be received by therapy module 120 directly from radiotherapy device 150. In some embodiments, testing data may be retrieved from radiotherapy device 150 in an online mode while radiotherapy device 150 is in active operation of performing radiotherapy treatment (e.g., actual dose delivered to a patient). In other embodiments, testing data may be retrieved from radiotherapy device 150 in an offline mode, e.g., while radiotherapy device 150 is not in active operation of performing radiotherapy treatment.

A therapy model can represent a dose distribution calculation given a training model and testing data. For example, the therapy model receives a noisy or short Monte Carlo simulation of a dose distribution calculation, an approximate deterministic dose calculation (e.g., pencil beam or collapsed cone) and uses the training model to enhance the received dose calculation to improve its accuracy and reduce the presence of noise. In some embodiments, a therapy model can be determined directly from training data and testing data. A therapy model can be a single model or a plurality of models. In some embodiments, a therapy model can be an output of therapy module 120. In other embodiments, a therapy model can be stored (e.g., in memory, training database 130, or testing database 140) for later retrieval. Storage of the therapy model allows for faster retrieval when determining further treatment plans. In some embodiments, a therapy model can be generated by treatment planning system 170 or training module 110. In other embodiments, the therapy model can be sent to treatment planning system 170 or training module 110. Determining the one or more therapy model can be performed either offline or online. For example, the therapy model can be determined and stored before beginning the treatment process (e.g., offline) or the therapy model can be estimated in real-time during the treatment process (e.g., online). In some embodiments, the therapy model can use testing data from a patient undergoing current radiotherapy treatment.

In some embodiments, the treatment planning system 170 can use the therapy model generated by therapy module 120 and an optimization model to determine an optimal or improved spatial distribution of a derived target vector. In other embodiments, therapy module 120 can generate the therapy model and use the optimization model to generate a treatment plan.

In some examples, the developed treatment plan can be for a patient currently undergoing radiotherapy (e.g., the treatment plan may be updated (adapted) based on current parameters). Alternatively, the developed treatment plan can be for a new patient. The treatment plan can be used by radiotherapy device 150 to perform a treatment in accordance with the treatment plan. Specifically, during radiotherapy planning, volumetric elements are delineated to be targeted or avoided with respect to the administration of a radiation dose. Once the PTV has been defined, and the OAR 420s have been identified, a responsible clinician can specify a desired radiation dose to the PTV and the allowable dose to OAR 420s. The planning software can then produce a treatment plan that attempts to meet the clinical dosimetric objectives. The treatment plan is the programmed set of instructions to the radiation delivery machine, but can be summarized for its clinical effect on the patient in terms of dose-volume relationships that can include a three-dimensional dose matrix. One commonly used embodiment of a dose-volume relationship is the dose-volume histogram (DVH) that summarizes the frequency distribution of radiation doses in a particular PTV or OAR structure. The dose deposition pattern can include a quantity of radiation provided to the one or more volume elements of the patient.

Radiotherapy device 150 delivers a beam or beams of high-energy radiation directed towards a tumor site (or other lesion) in a controlled manner according to a treatment plan. A multiple-source external-beam radiotherapy device uses a large number of fixed sources, often isotopic sources such as Cobalt-60 which decays via a process including gamma emission. The sources can be mounted in an approximately hemispherical collimator arrangement which collimates each source to direct its radiation to the center of the hemisphere. Thus, at that center point the radiation fluence is very high, whereas away from that point the fluence drops markedly. Individual sources can be blocked or opened to allow irradiation. A patient can therefore be positioned (with all sources blocked), and a selection of sources can then be opened for a specified time to create a high fluence at a specific location within the patient and deliver a specific dose. A tumor might be exposed to several "shots" (which may be at different locations) in order to fill up the target volume with the prescribed dose level. Also, several tumor sites can be treated in one treatment.

Figure 2:
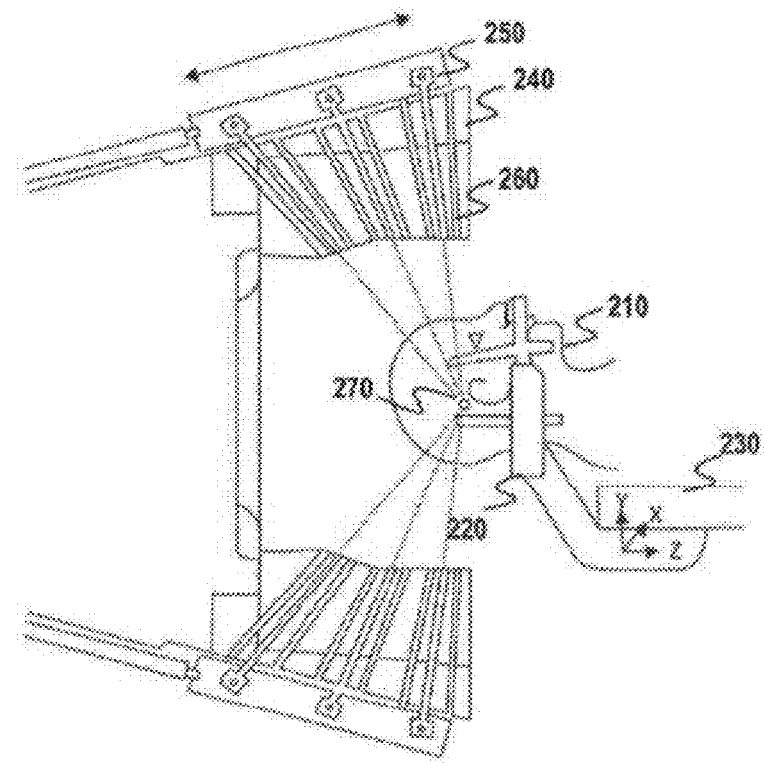
FIG. 2 illustrates an illustrative radiotherapy device, according to some examples of the disclosure.

FIG. 2 illustrates a Leksell Gamma Knife 200, one type of multiple-source external-beam type of radiotherapy device 150, according to some embodiments of the present disclosure. As shown in FIG. 2, in a radiotherapy treatment session, a patient 210 may wear a coordinate frame 220 to keep stable the patient 210's body part (e.g., the head) undergoing surgery or radiotherapy. In some examples, coordinate frame 220 and a patient positioning system 230 establish a spatial coordinate system, which can be used while imaging a patient 210 or during radiation surgery. In some embodiments, radiotherapy device 150 includes a protective housing 240 to enclose a plurality of radiation sources 250. Radiation sources 250 generate a plurality of radiation beams (e.g., beamlets) through beam channels 260. The plurality of radiation beams can be configured to focus on an isocenter 270 from different directions. While each individual radiation beam can have a relatively low intensity, isocenter 270 can receive a relatively high level of radiation when multiple doses from different radiation beams accumulate at isocenter 270. In certain embodiments, isocenter 270 corresponds to a target under surgery or treatment, such as a tumor.

A single-source external-beam radiotherapy device uses a beam of radiation (e.g., in the MeV range, apt to damage tumor cells), and directs the beam towards the patient 210. The source is movable so as to allow a range of irradiation directions to be chosen, and the lateral extent of the beam is limited by collimating elements so as to match a pattern determined in a predetermined treatment plan, such as the external profile of the tumor or a subsection of it. The direction of the beam is varied so that the tumor is irradiated from multiple directions, thereby reducing the dose delivered to tissue surrounding the tumor site.

Figure 3:
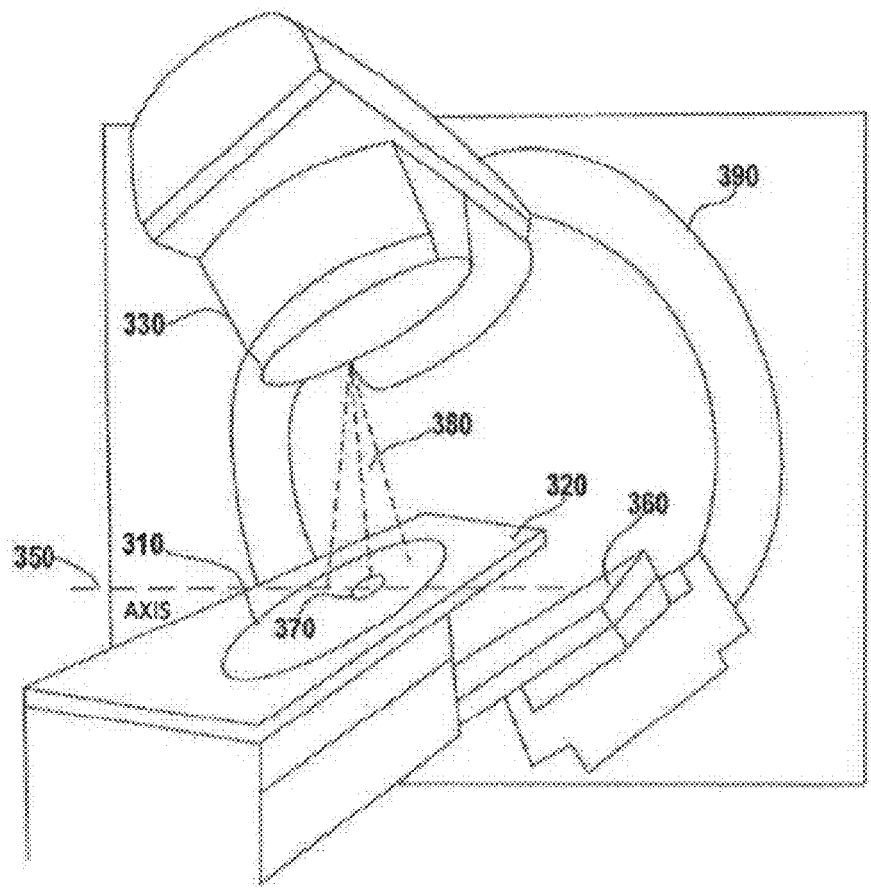
FIG. 3 illustrates another example radiotherapy device, such as a linear accelerator.

FIG. 3 illustrates a linear accelerator 300, a single-source external-beam type of radiotherapy device 150, according to some embodiments of the present disclosure. Using linear accelerator 300, a patient 310 can be positioned on a patient table 320 to receive a radiation dose determined by the treatment plan. In some embodiments, linear accelerator 300 includes a radiation head 330 that generates a radiation beam 380. The entire radiation head 330 can be rotatable around a horizontal axis 350. In some examples, a flat panel detector 360 is located below the patient table 320, which can rotate synchronously with radiation head 330 around an isocenter 370. The intersection of the axis 350 with the center of the beam 380, produced by the radiation head 330, is usually referred to as "isocenter." The patient table 320 can be motorized so that the patient 310 can be positioned with the tumor site at or close to the isocenter 370. The radiation head 330 can rotate about a gantry 390, to provide patient 310 with a plurality of varying dosages of radiation according to the treatment plan.

Internal radiotherapy (e.g., brachytherapy) involves placing a sealed radiation source in or adjacent to the area requiring treatment. Radiation is then delivered directly to the lesion site. The principal form of control is obtained from the positioning of the source relative to the site, but the source strength parameters can also be controlled using a treatment plan.

Figure 4:
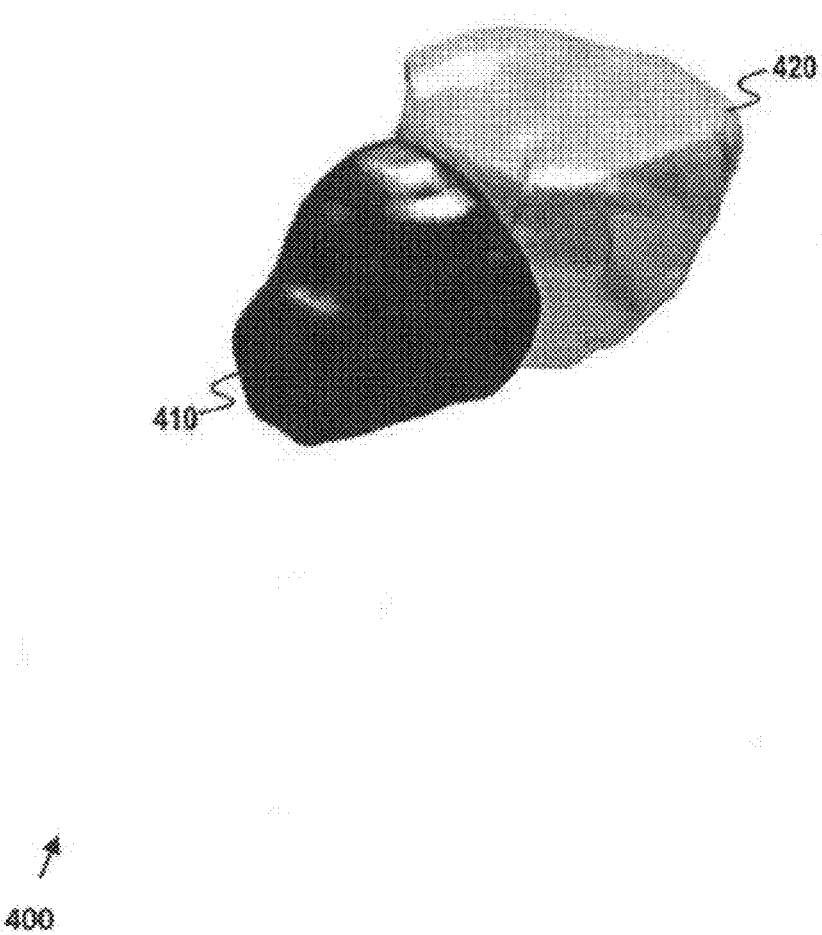
FIG. 4. illustrates an example volume rendering of structures segmented on some imaging data.

FIG. 4 illustrates an example volume rendering of structures segmented on some imaging data, for example, acquired by image acquisition device 160. In the example, target 410 can be a PTV (e.g., tumor, and the like) and an OAR 420 can be an organ near the target 410. The PTV can have an irregular volume and may be unique as to its size, shape, and position. In order to delineate the target 410 from the OAR 420, medical images (e.g., MRI images, CT images, PET images, fMRI images, X-ray images, ultrasound images, radiotherapy portal images, SPECT images, and the like) of the patient undergoing radiotherapy can be obtained non-invasively and segmented to include voxels. Each voxel represents a spatial volume in the image data. It is noted that target 410 and OAR 420 shown in FIG. 4 represent a 3D reconstruction of a segmented target 410 and OAR 420. In some examples, a 3D structure, such as the one shown in FIG. 4, is produced by segmenting image data acquired by image acquisition device 160.

In certain embodiments, the 3D structure of a PTV or an OAR 420 can be generated automatically by either training module 110, therapy module 120, and/or stored in training database 130 or testing database 140. In addition, if the PTV is close to the OAR 420 (e.g., prostate in near proximity to the bladder and rectum), segmentation of the OAR 420 can allow study of the dose distribution not only in the PTV, but also in the OAR 420. In some examples, radiation doses to be applied to a PTV (e.g., a target tumor) and any OAR 420 proximate to the tumor (e.g., left and right parotid, optic nerves, eyes, lens, inner ears, spinal cord, brain stem, and the like) can be determined after segmentation.

Figure 5:
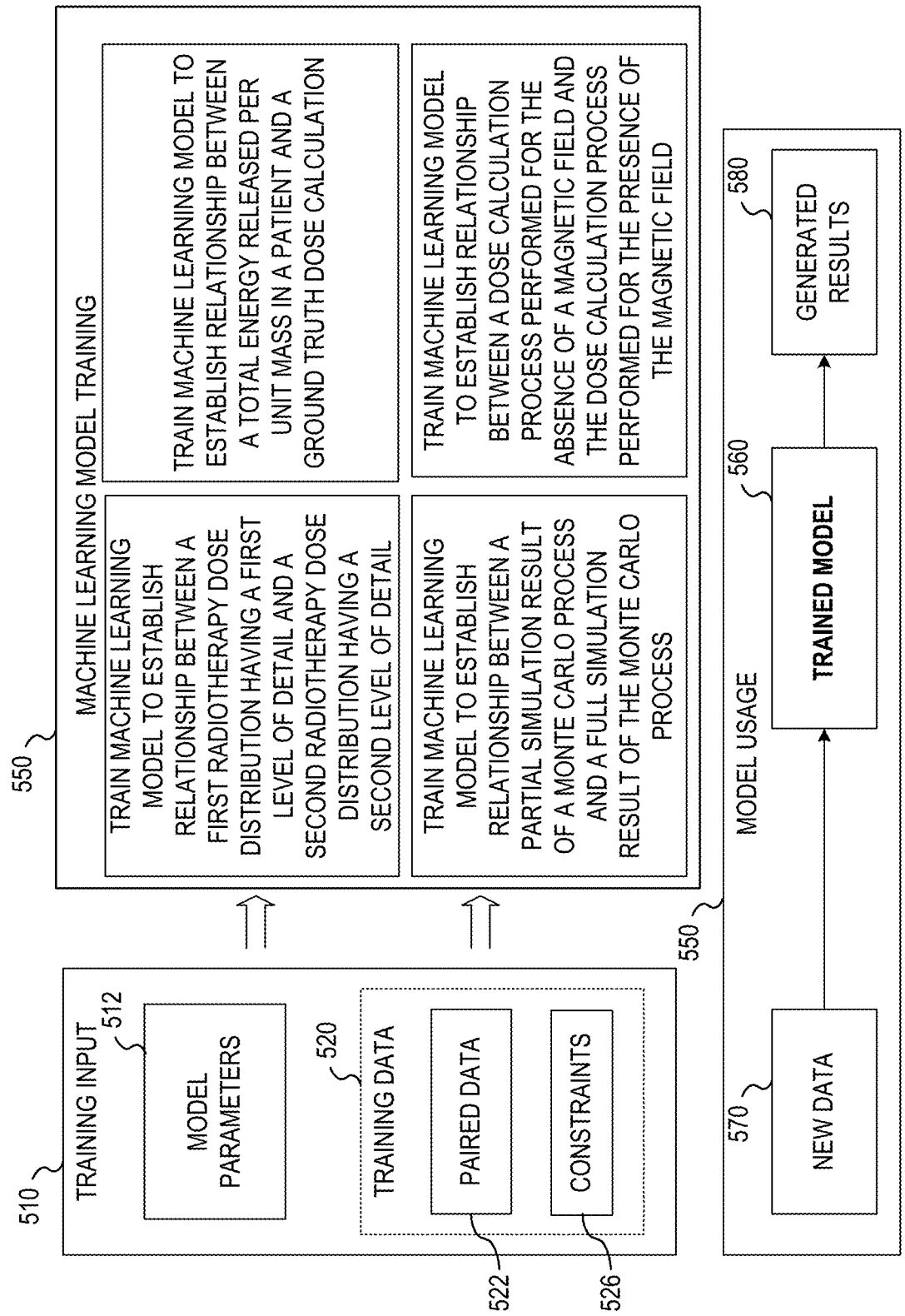
FIG. 5 illustrates an exemplary data flow for training and use of a machine learning technique, according to some examples of the disclosure.

FIG. 5 illustrates an exemplary data flow for training and use of a machine learning model, according to some examples of the disclosure. The data flow includes training input 510, ML model (technique) training 530, and model usage 550.

Training input 510 includes model parameters 512 and training data 520, which may include paired training data sets 522 (e.g., input-output training pairs) and constraints 526. Model parameters 512 store or provide the parameters or coefficients of machine learning model $\hat{A}_\theta$. During training, these parameters 512 are adapted based on the input-output training pairs of the training data sets 522. After the parameters 512 are adapted (after training), the parameters 512 are used by trained treatment models 560 to implement the trained machine learning model $\hat{A}_\theta$ on a new set of data 570.

Training data 520 includes constraints 526, which may define the physical constraints of a given radiotherapy device 150. The paired training data sets 522 may include sets of input-output pairs, such as pairs of a radiation dose computation representing total energy released per unit mass in a patient 310 and a ground truth dose calculation; a radiotherapy dose distribution having a first level of detail and a ground truth dose distribution having a second level of detail; a partial simulation result of a Monte Carlo process and a ground truth full simulation result of the Monte Carlo process; a dose calculation process performed for the absence of a magnetic field and a ground truth dose calculation process performed for the presence of the magnetic field; or any combination thereof. Some components of training input 510 may be stored separately at a different off-site facility or facilities than other components.

Machine learning model(s) training 530 trains one or more machine learning techniques $\hat{A}_\theta$ based on the sets of input-output pairs of paired training data sets 522. For example, the model training 530 may train the ML model parameters 512 by minimizing a first loss function based on radiation dose computation representing total energy released per unit mass in a patient 310 and the corresponding ground truth dose calculation; a radiotherapy dose distribution having a first level of detail and the corresponding ground truth dose distribution having a second level of detail; a partial simulation result of a Monte Carlo process and the corresponding ground truth full simulation result of the Monte Carlo process; a dose calculation process performed for the absence of a magnetic field and the corresponding ground truth dose calculation process performed for the presence of the magnetic field.

The result of minimizing the loss function for multiple sets of training data 520 trains, adapts, or optimizes the model parameters 512 of the corresponding ML models. In this way, the ML model is trained to establish a relationship between first radiotherapy dose distribution having the first level of detail and a radiotherapy dose distribution having a second level of detail that enhances the first level of detail.

As an example, a first ML model may be trained according to supervised learning techniques. In such cases, to train the first ML model $\Lambda_\theta$, a plurality of radiotherapy dose distribution calculations having the first level of detail are retrieved together with their corresponding ground truth radiotherapy dose distribution calculation having a second level of detail. Specifically, a first training data 520 batch that includes a batch of radiotherapy dose distribution calculations having a first level of detail and the corresponding batch of ground truth dose distribution calculations having a second level of detail is obtained. The batch of the training data 520 can be used to train the first ML model with the same parameters of the first ML model. The given batch of the dose distribution calculations having the first level of detail is processed with the first ML model to generate the estimate of the dose distribution calculations having the second level of detail. A deviation is computed between the estimate of the radiotherapy dose distribution having the second level of detail and the ground truth radiotherapy dose distribution having the second level of detail. Parameters 512 of the machine learning model are updated based on the computed deviation.

The first ML model is then applied with the updated parameters to another batch of the training data 520 to again estimate dose distribution calculations having the second level of detail to compute a deviation in a similar manner as the first batch and update parameters 512 of the ML model. Parameters 512 of the ML model are again updated and iterations of this training process continue for a specified number of iterations or epochs or until a given convergence criteria has been met.

A second ML model may be trained in a similar manner as the first ML model to establish a relationship between a total energy released per unit mass in a patient 310 and a ground truth dose calculation. For example, the second ML model may be trained based on training data 520 to establish a relationship between a computation representing total energy released per unit mass in a patient 310 and a ground truth dose calculation that is generated by applying a point kernel convolution process consisting of calculating the total energy released per unit mass in a patient 310 and a subsequent point kernel convolution step to the training data set. In this case, when only a total released energy in a patient 310 (e.g., a new total released energy calculation) is received by the second ML model from a given dose calculation process (e.g., a point kernel convolution process), the second ML model estimates the corresponding dose calculation that is close to the ground truth dose calculation that includes the convolution step. Particularly, the point kernel convolution process can be applied to a set of data without applying the convolution step to generate a first radiotherapy treatment dose having a first level of detail. Then the therapy module 120, using the second ML model, processes the first radiotherapy treatment dose distribution to generate a second radiotherapy treatment dose distribution having a second level of detail that, for example, is an estimate of applying the convolution step of the point kernel convolution process.

A third ML model may be trained in a similar manner as the first ML model to establish a relationship between a partial simulation result of a Monte Carlo process and a full simulation result of the Monte Carlo process. For example, the third ML model may be trained based on training data 520 to establish a relationship between a partial simulation result of the Monte Carlo process and a full simulation result of the Monte Carlo process. In this case, when noisy dose calculations are received by the third ML model from a given dose calculation process (e.g., a Monte Carlo simulation that was terminated prematurely), the third ML model estimates the corresponding dose calculation that is close to the full Monte Carlo simulation on the data and is less noisy. Particularly, the Monte Carlo simulation can be applied to a set of data and terminated prematurely to generate a first radiotherapy treatment dose distribution having a first level of detail (e.g., data that is suboptimal and noisy). Then the therapy module 120, using the third ML model, processes the first radiotherapy treatment dose distribution to generate a second radiotherapy treatment dose distribution having a second level of detail that, for example, is an estimate of applying the full Monte Carlo simulation that denoises the data. In such implementations, the third ML model may include a neural network (e.g., a convolutional neural network and/or a denoising autoencoder).

A fourth ML model may be trained in a similar manner as the first ML model to establish a relationship between a dose calculation process performed for the absence of a magnetic field and the dose calculation process performed for the presence of the magnetic field. For example, the fourth ML model may be trained based on training data 520 to establish a relationship between the dose calculation process performed in the absence of a magnetic field and the dose calculation process performed in the presence of the magnetic field. In this case, when dose calculations are received by the fourth ML model from a given dose calculation process (e.g., a Monte Carlo algorithm) and/or from an output of another trained machine learning technique that has denoised the dose calculation provided by a given dose calculation process, the fourth ML model estimates the corresponding dose distribution calculation in the presence of a magnetic field.

Any of the first, second, third, or fourth ML models may be further trained based on one or more additional radiotherapy dose distributions generated using another dose calculation process, patient geometry information, and beam setup information. Namely, the training data 520 may include dose calculations that adjust or account for patient geometry, one or more additional radiotherapy dose distributions generated using another dose calculation process, and beam setup information. In some embodiments, the first, second, third, or fourth ML models may be trained to establish the relationships based on a single beam and are subsequently further trained to establish the relationships based on multiple beams.

After the machine learning models $\hat{A}_\theta$ (sometimes referred to as $\Lambda_\theta$) are trained, new data 570, including one or more dose calculations having a first level of detail, may be received. The trained machine learning techniques $\hat{A}_\theta$ may be applied to the new data 570 to generate generated results 580 including one or more estimated dose calculations having a second level of detail.

Figure 6:
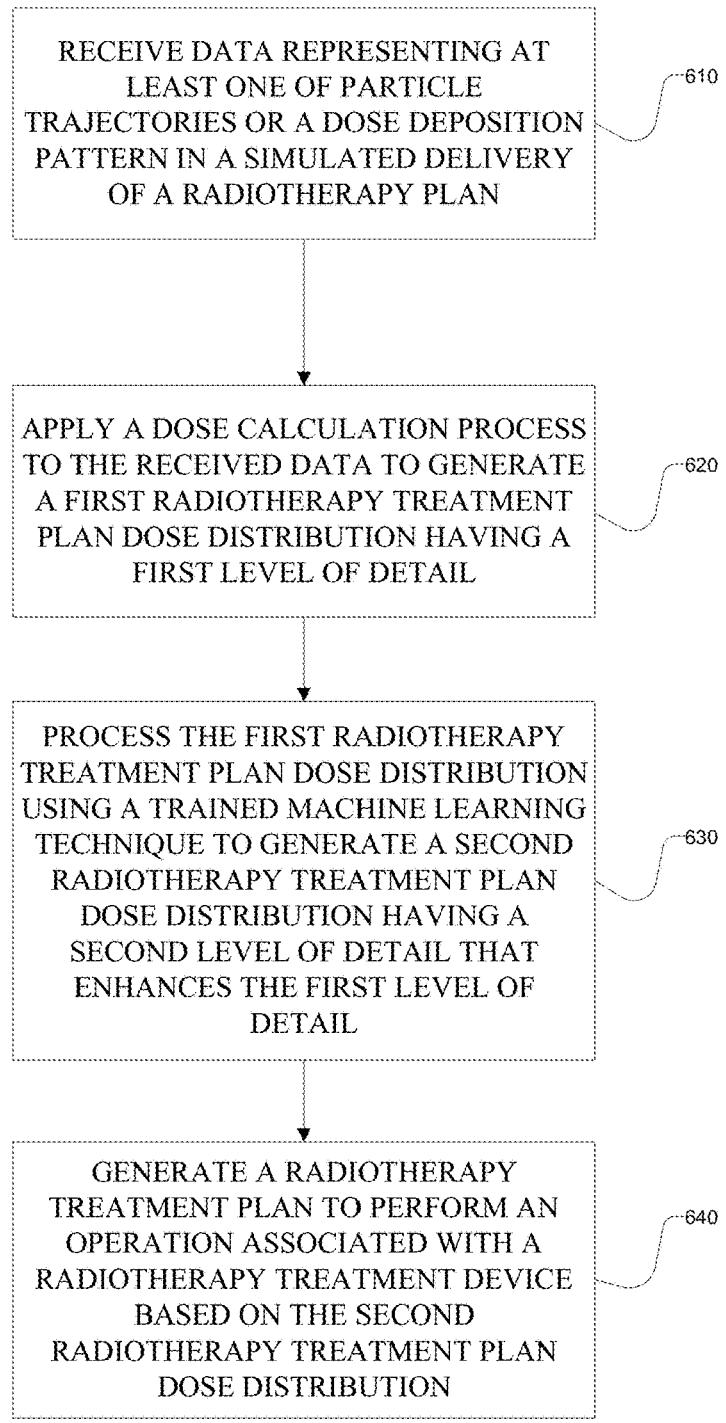
FIG. 6 illustrates an example flowchart of a process for computing a radiotherapy dose distribution for a patient, according to some examples of the disclosure.

FIG. 6 is a flowchart of an illustrative process 600 of computing a radiotherapy dose distribution for a patient 310 and can be implemented, for example, in a system shown in FIG. 1. The technologies described herein are consistent with different operating systems or hardware and can be applied in any variety of environments to take advantage of the described features.

At block 610, the therapy module 120 receives data representing at least one of particle trajectories or a dose deposition pattern in a simulated delivery of a radiotherapy plan.

At block 620, the therapy module 120 applies a dose calculation process to the received data to generate a first radiotherapy dose distribution having a first level of detail.

At block 630, the therapy module 120 processes the first radiotherapy dose distribution using a trained machine learning technique to generate a second radiotherapy dose distribution having a second level of detail that enhances the first level of detail.

At block 540, the therapy module 120 generates a radiotherapy treatment plan to perform an operation associated with a radiotherapy treatment device based on the second radiotherapy dose distribution.

Figure 7:
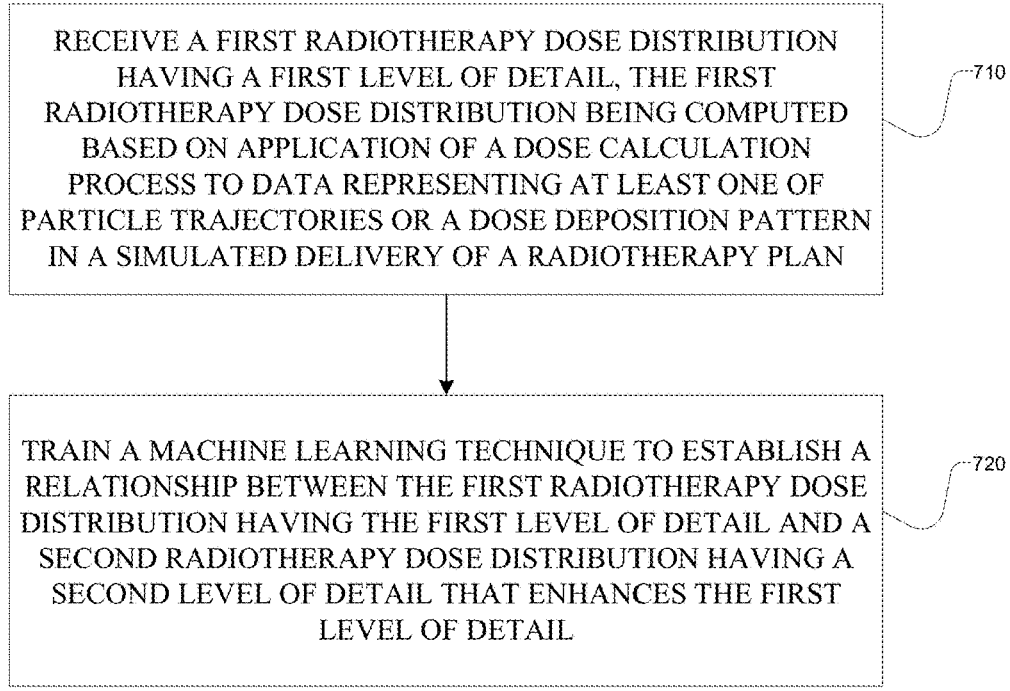
FIG. 7 illustrates an example flowchart of a process for training a machine learning technique, according to some examples of the disclosure.

FIG. 7 is a flowchart of an illustrative process 700 for training a machine learning technique, for example, in a system shown in FIGS. 1 and 5. The technologies described herein are consistent with different operating systems or hardware and can be applied in any variety of environments to take advantage of the described features.

At block 710, the therapy module 120 receives a first radiotherapy dose distribution having a first level of detail, the first radiotherapy dose distribution being computed based on application of a dose calculation process to data representing at least one of particle trajectories or a dose deposition pattern in a simulated delivery of a radiotherapy plan.

At block 720, the therapy module 120 trains a machine learning technique to establish a relationship between the first radiotherapy dose distribution having the first level of detail and a second radiotherapy dose distribution having a second level of detail that enhances the first level of detail.

The technologies described herein have many advantages in the field of radiation therapy or radiotherapy. For example, computing a treatment plan dose distribution as described herein can significantly reduce computational time and required memory.

Additional Notes

As previously discussed, respective electronic computing systems or devices may implement one or more of the methods or functional operations as discussed herein. In one or more embodiments, the radiotherapy processing computing system may be configured, adapted, or used to control or operate the image-guided radiation therapy device, perform or implement the operations of the above processes, or perform any one or more of the other methodologies discussed. In various embodiments, such electronic computing systems or devices operates as a standalone device or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a personal digital assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine readable medium. While the machine-readable medium may have been described in various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present disclosure, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present disclosure also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and example parameters, functions, and implementations described herein are intended to define the parameters of the disclosure, they are by no means limiting and are illustrative embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled.

What is claimed is:

1. A computer implemented method for calculating radiotherapy dose distribution, the method comprising:
   receiving data representing at least one of particle trajectories or a dose deposition pattern in a simulated delivery of a radiotherapy plan;
   applying a dose calculation process to the received data to generate a first radiotherapy dose distribution having a first level of detail; and
   processing the first radiotherapy dose distribution using a trained machine learning technique to generate a second radiotherapy dose distribution having a second level of detail that enhances the first level of detail; and
   wherein the dose calculation process includes one or more operations that are prematurely stopped or skipped over, before convergence to the second level of detail, to generate the first radiotherapy dose distribution.

2. The method of claim 1, further comprising generating a radiation dose distribution or treatment plan to perform an operation associated with a radiotherapy treatment device based on the second radiotherapy dose distribution, wherein the operation includes at least one of delivering radiotherapy using the radiotherapy treatment device or verifying proper operation of the radiotherapy treatment device in real-time during treatment.

3. The method of claim 1, wherein the particle includes at least one of a photon, proton, electron or ion, and wherein the dose calculation process applied to generate the first radiotherapy dose distribution includes at least one or a combination of a Monte Carlo simulation or a deterministic calculation using a point kernel convolution algorithm, a pencil kernel algorithm, or a Boltzmann equation solver.

4. The method of claim 1, wherein the data includes multiple single particle simulations, wherein the data includes at least one or a combination of a mean-free path parameter, interaction type parameter, deposited energy parameter, and wherein the particle trajectories represent post direction of travel sampled from one or more specified distributions or one or more distributions specified up to a specified value.

5. The method of claim 1, wherein the dose calculation process includes a Monte Carlo simulation that is prematurely stopped before convergence to the second level of detail, where convergence is measured using a measure of statistical dispersion, and wherein the first dose distribution has a higher measure of statistical dispersion than the second dose distribution.

6. The method of claim 1, wherein the dose calculation process comprises a point kernel convolution process that includes a ray trace step and a convolution step, further comprising:
applying a dose calculation process to the received data comprises computing an amount representing a total energy released per unit mass in a patient based on the received data using a ray trace process; and
without requiring performing the convolution step modeling transport and dose deposition of photons and electrons generated by the incident photons, based on the trained machine learning technique to generate the second radiotherapy dose distribution.

7. The method of claim 1, wherein the second radiotherapy distribution represents a dose from individual beamlets or shots.

8. The method of claim 1, wherein prematurely stopping or skipping over the one or more operations of the dose calculation process results in generating the first radiotherapy dose distribution for the absence of a magnetic field, wherein the second radiotherapy dose distribution is generated, based on the first radiotherapy dose distribution, for the presence of the magnetic field, further comprising generating a complete dose plan based on the second radiotherapy dose distribution for a given radiotherapy machine configuration.

9. The method of claim 1, wherein the second radiotherapy dose distribution represents an external radiation field associated with a radiotherapy treatment device, further comprising:
determining an amount of radiation associated with the radiotherapy treatment device or treatment room; and
based on the amount of radiation, performing at least one of estimating patient motion, configuring a radiation shield, or computing a beam model associated with the radiotherapy treatment device.

10. The method of claim 1, wherein the machine learning technique comprises a neural network.

11. The method of claim 10, wherein the neural network comprises at least one of a convolutional neural network and a denoising autoencoder, wherein the first radiotherapy dose distribution is represented as a three-dimensional image, and wherein processing the first radiotherapy dose distribution using the trained machine learning technique further comprises providing the first radiotherapy dose distribution, one or more additional radiotherapy dose distributions generated using the dose calculation process, patient geometry information, and beam setup information to the trained machine learning technique.

12. The method of claim 1, wherein the dose calculation process comprises a point kernel convolution process, and wherein the trained machine learning technique is trained based on training data to establish a relationship between a computation representing total energy released per unit mass in a patient and a ground truth dose calculation.

13. The method of claim 12, wherein the training data comprises sets of input-output data pairs, wherein the ground truth dose calculation is generated by applying the point kernel convolution process including a raytracing step and a convolution step to the training data set, and wherein the input portion of the input-output data pairs comprises a patient model.

14. The method of claim 1, wherein the machine learning technique is trained based on a single beam and is subsequently further trained based on multiple beams.

15. The method of claim 1, wherein the dose calculation process comprises a Monte Carlo process, and wherein the trained machine learning technique is trained based on training data to establish a relationship between a partial simulation result of the Monte Carlo process and a full simulation result of the Monte Carlo process.

16. The method of claim 1, wherein the dose calculation process is performed for the absence of a magnetic field, and wherein the trained machine learning technique is trained based on training data to establish a relationship between the dose calculation process performed for the absence of a magnetic field and the dose calculation process performed for the presence of the magnetic field.

17. The method of claim 1, wherein the dose calculation process includes a differentiable process, and wherein the machine learning technique comprises a differentiable machine learning technique.

18. The method of claim 1, wherein the first level of detail represents at least one of or a combination of a first level of noise, a suboptimal input image, or a dose distribution in the absence of a magnetic field, and wherein the second level of detail represents at least one or a combination of a second level of noise less than the first level of detail, an improved input image or the dose distribution in the presence of a magnetic field.

19. A system for calculating radiotherapy dose distribution, the system comprising:
one or more processors configured to perform operations comprising:
receiving data representing at least one of particle trajectories or a dose deposition pattern in a simulated delivery of a radiotherapy plan;
applying a dose calculation process to the received data to generate a first radiotherapy dose distribution having a first level of detail; and
processing the first radiotherapy dose distribution using a trained machine learning technique to generate a second radiotherapy dose distribution having a second level of detail that enhances the first level of detail, wherein the dose calculation process includes one or more operations that are prematurely stopped or skipped over, before convergence to the second level of detail, to generate the first radiotherapy dose distribution.

20. The system of claim 19, wherein the operations further comprise generating a radiation dose distribution or treatment plan to perform an operation associated with a radiotherapy treatment device based on the second radiotherapy dose distribution, wherein the operation includes at least one of delivering radiotherapy using the radiotherapy treatment device or verifying proper operation of the radiotherapy treatment device in real-time during treatment.

21. The system of claim 19, wherein the trained machine learning technique is trained based on training data to establish a relationship between one or a combination of a computation representing total energy released per unit mass in a patient and a ground truth dose calculation; a partial simulation result of a Monte Carlo process and a full simulation result of the Monte Carlo process; and the dose calculation process performed for the absence of a magnetic field and the dose calculation process performed for the presence of the magnetic field.

22. A computer implemented method for training a machine learning technique, the method comprising:
   receiving a first radiotherapy dose distribution having a first level of detail, the first radiotherapy dose distribution being computed based on application of a dose calculation process to data representing at least one of particle trajectories or a dose deposition pattern in a simulated delivery of a radiotherapy plan; and
   training a machine learning technique to establish a relationship between the first radiotherapy dose distribution having the first level of detail and a radiotherapy dose distribution having a second level of detail that enhances the first level of detail, wherein the dose calculation process includes one or more operations that are prematurely stopped or skipped over, before convergence to the second level of detail, to generate the first radiotherapy dose distribution.

23. The method of claim 22, wherein the machine learning technique is trained based on training data to establish a relationship between one or a combination of a computation representing total energy released per unit mass in a patient and a ground truth dose calculation; a partial simulation result of a Monte Carlo process and a full simulation result of the Monte Carlo process; and the dose calculation process performed for the absence of a magnetic field and the dose calculation process performed for the presence of the magnetic field.

24. The method of claim 22, wherein the first level of detail represents at least one of or a combination of a first level of noise, a suboptimal input image, or a dose distribution in the absence of a magnetic field, and wherein the second level of detail represents at least one or a combination of a second level of noise less than the first level of detail, an improved input image or the dose distribution in the presence of a magnetic field.

25. The method of claim 22, wherein the machine learning technique is trained by:
   obtaining a training data pair comprising a training radiotherapy dose distribution having the first level of detail and a corresponding ground truth radiotherapy dose distribution having the second level of detail;
   processing the training radiotherapy dose distribution having the first level of detail with the machine learning technique to generate an estimate of the training radiotherapy dose distribution having the second level of detail;
   computing a deviation between the estimate of the training radiotherapy dose distribution having the second level of detail and the ground truth radiotherapy dose distribution having the second level of detail; and
   updating parameters of the machine learning model based on the computed deviation.

26. A system for training a machine learning technique, the system comprising:
   one or more processors configured to perform operations comprising:
   receiving a first radiotherapy dose distribution having a first level of detail, the first radiotherapy dose distribution being computed based on application of a dose calculation process to data representing at least one of particle trajectories or a dose deposition pattern in a simulated delivery of a radiotherapy plan; and
   training a machine learning technique to establish a relationship between the first radiotherapy dose distribution having the first level of detail and a second radiotherapy dose distribution having a second level of detail that enhances the first level of detail, wherein the dose calculation process includes one or more operations that are prematurely stopped or skipped over, before convergence to the second level of detail, to generate the first radiotherapy dose distribution.

27. The system of claim 26, wherein the machine learning technique is trained based on training data to establish a relationship between one or a combination of a computation representing total energy released per unit mass in a patient and a ground truth dose calculation; a partial simulation result of a Monte Carlo process and a full simulation result of the Monte Carlo process; and the dose calculation process performed for the absence of a magnetic field and the dose calculation process performed for the presence of the magnetic field.

28. The method of claim 26, wherein the first level of detail represents at least one of or a combination of a first level of noise, a suboptimal input image, or a dose distribution in the absence of a magnetic field, and wherein the second level of detail represents at least one or a combination of a second level of noise less than the first level of detail, an improved input image or the dose distribution in the presence of a magnetic field.

29. The method of claim 26, wherein the machine learning technique is trained by:
   obtaining a training data pair comprising a training radiotherapy dose distribution having the first level of detail and a corresponding ground truth radiotherapy dose distribution having the second level of detail;
   processing the training radiotherapy dose distribution having the first level of detail with the machine learning technique to generate an estimate of the training radiotherapy dose distribution having the second level of detail;
   computing a deviation between the estimate of the training radiotherapy dose distribution having the second level of detail and the ground truth radiotherapy dose distribution having the second level of detail; and
   updating parameters of the machine learning model based on the computed deviation.

* * * * *